United States Patent [19]

Kopfer

[11] Patent Number: 5,584,819
[45] Date of Patent: Dec. 17, 1996

[54] NESTED BLUNT/SHARP INJECTION ASSEMBLY

[76] Inventor: Rudolph J. Kopfer, 131 Sage Rd., Hulen Meadows, Ketchum, Id. 83340

[21] Appl. No.: 403,213

[22] Filed: Mar. 13, 1995

[51] Int. Cl.$^6$ .............................. A61M 5/00; A61M 5/31
[52] U.S. Cl. .......................... 604/239; 604/272; 604/411
[58] Field of Search .......................... 604/239, 272–274, 604/905, 200, 201, 192, 198, 56, 80, 82, 83, 87, 88, 92, 407, 408, 410, 411, 412, 240, 242, 243, 117; 215/DIG. 3; 141/27, 329, 330

[56] References Cited

U.S. PATENT DOCUMENTS

| Re. 34,845 | 1/1995 | Vetter et al. | 604/243 |
|---|---|---|---|
| 4,185,628 | 1/1980 | Kopfer . | |
| 4,201,208 | 5/1980 | Cambio, Jr. | 141/329 X |
| 4,516,967 | 5/1985 | Kopfer | 604/87 |
| 4,619,651 | 10/1986 | Kopfer et al. | 604/415 |
| 4,775,369 | 10/1988 | Schwartz | 604/263 |
| 4,804,372 | 2/1989 | Laico et al. | 604/198 |
| 4,826,488 | 5/1989 | Nelson et al. | 604/192 |
| 4,834,718 | 5/1989 | McDonald | 604/195 |
| 4,850,996 | 7/1989 | Cree | 604/198 |
| 4,872,552 | 10/1989 | Unger | 206/365 |
| 4,978,344 | 12/1990 | Dombrowski | 604/198 |
| 5,015,240 | 5/1991 | Soproni et al. | 604/192 |
| 5,088,996 | 2/1992 | Kopfer et al. | 604/415 |
| 5,364,387 | 11/1994 | Sweeney | 604/411 |
| 5,411,499 | 5/1995 | Dudar et al. | 604/411 |
| 5,423,753 | 6/1995 | Fowles et al. | 604/87 |
| 5,474,546 | 12/1995 | Ambrisco et al. | 604/411 |
| 5,527,306 | 6/1996 | Haining | 604/411 |

FOREIGN PATENT DOCUMENTS

| 0268445 | 5/1988 | European Pat. Off. | A61M 5/32 |
|---|---|---|---|
| 0306606 | 3/1989 | European Pat. Off. | A61M 5/32 |
| 0409057 | 1/1991 | European Pat. Off. | A16M 5/158 |
| WO89/10151 | 11/1989 | WIPO | A61M 5/32 |

Primary Examiner—Corrine M. McDermott
Assistant Examiner—V. Alexander
Attorney, Agent, or Firm—Medlen & Carroll, LLP

[57] ABSTRACT

An injection device is provided which avoids the problems of coring, needle dulling, and accidental needle sticks which can occur when a conventional sharp hypodermic needle is used to access a medication vial. In this device a conventional sharp hypodermic needle having a conventional syringe attachment such as a Luer Lok adapter is nested inside a specially adapted blunt cannula which is provided with a sharp vial access tip. The above assembly is enclosed by a removable protective sheath, to protect the vial access tip and blunt cannula (as well as the sharp administration needle nested inside the blunt cannula) before and during use. In use, the protective sheath is removed and the vial access tip is used to penetrate the elastomeric stopper which conventionally seals a medication vial, thus protecting both the blunt cannula and the sharp needle from contact with the elastomeric stopper. The vial access tip can be removable, so that it remains behind in the medication vial after the syringe has been filled and the blunt cannula removed. The user can then selectively use either the blunt cannula or the sharp needle for administration of the medication. If the sharp needle is desired, the blunt cannula can be removed by replacing the protective sheath and engaging a locking mechanism between the protective sheath and the blunt cannula for separating the blunt cannula from the needle hub, thus exposing the sharp needle.

24 Claims, 3 Drawing Sheets

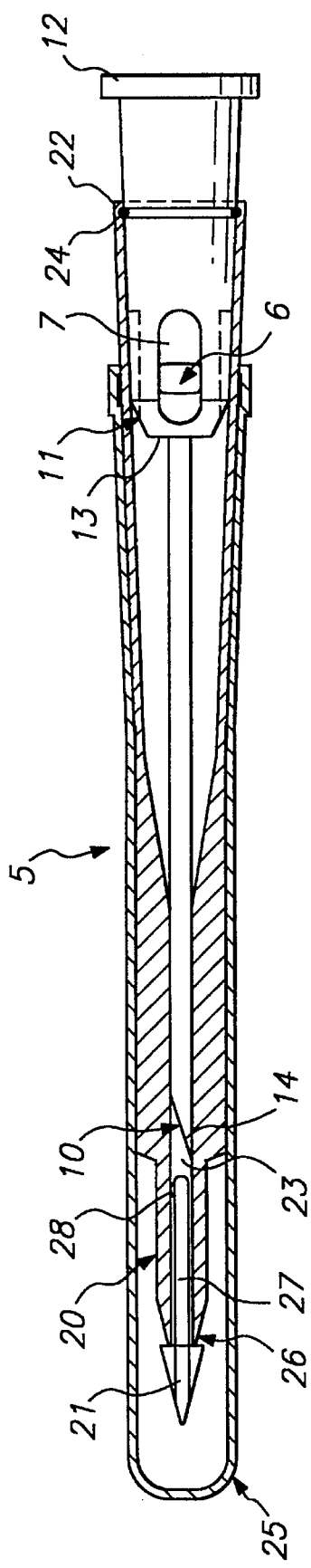
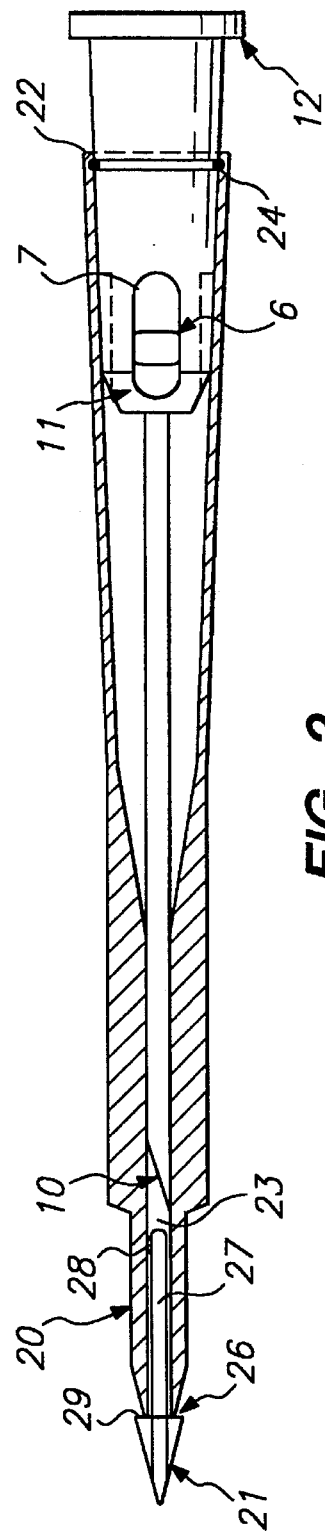

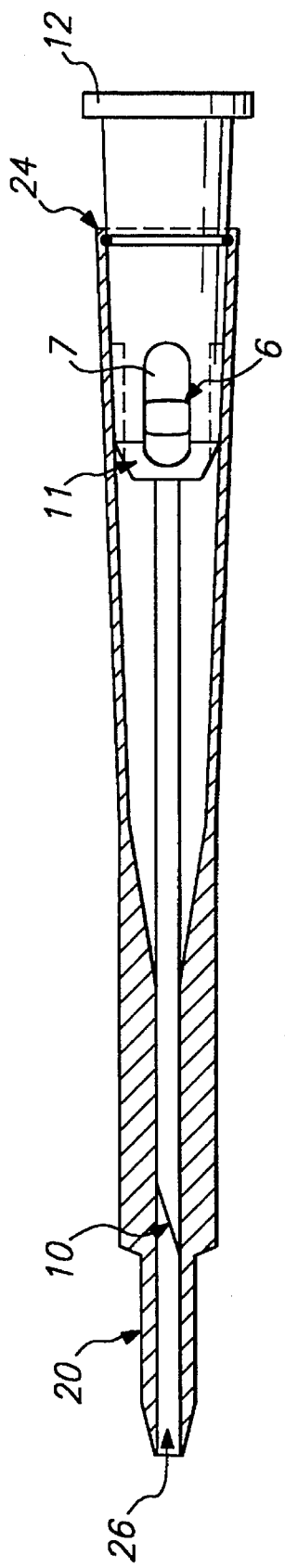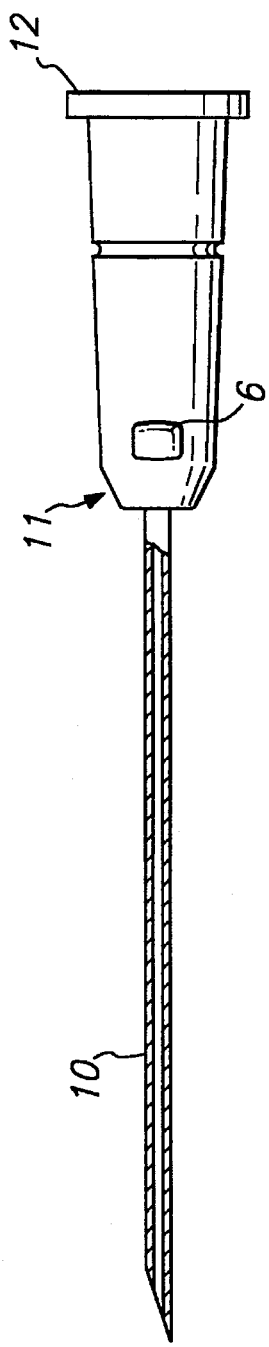
FIG. 3
FIG. 4

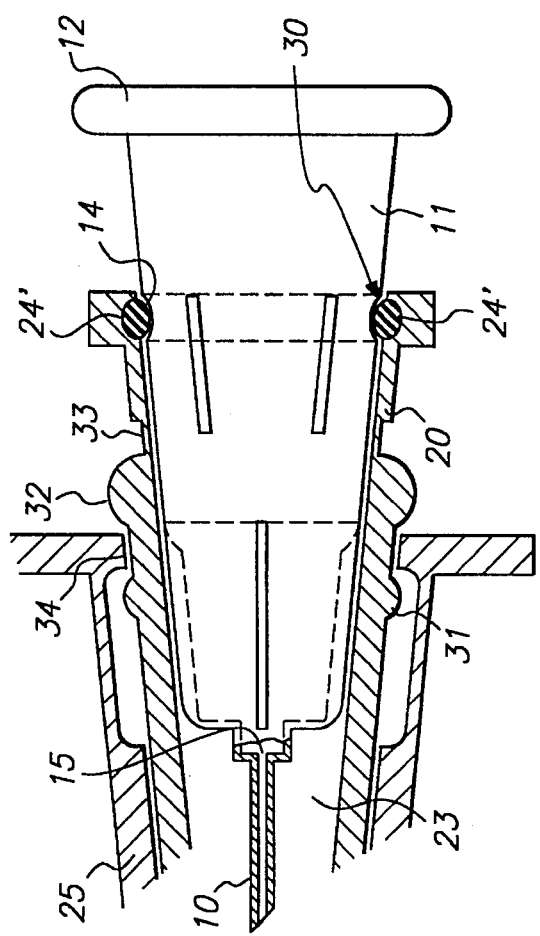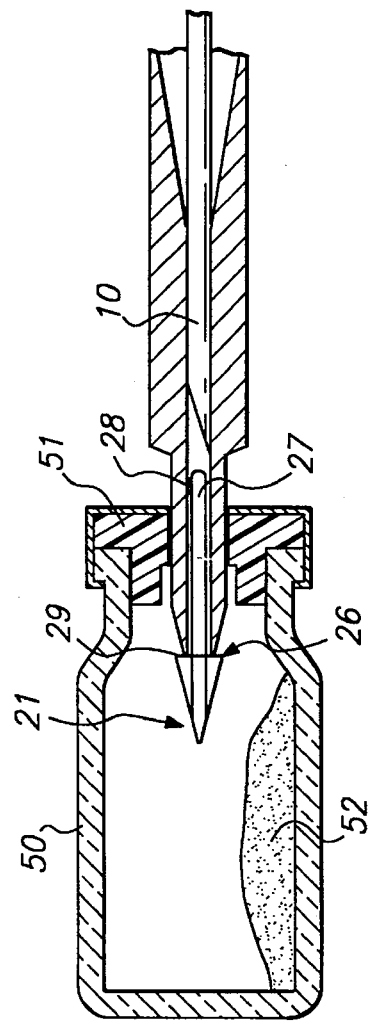

5,584,819

NESTED BLUNT/SHARP INJECTION ASSEMBLY

FIELD OF THE INVENTION

The present invention relates generally to the field of medical devices. More particularly, the present invention relates to hypodermic needles used to inject liquid medications into a body.

BACKGROUND OF THE INVENTION

The hypodermic needle, a hollow, pointed stainless steel cannula, attached to a syringe, is the standard medical device for giving injections to or withdrawing bodily fluids from a patient. However, this same needle and syringe can also be used by the health care worker to access and prepare the medication or injectant of choice prior to injection into the patient. This typically requires the insertion of the needle through an elastomeric stopper on standard medication vials.

Unfortunately, this obligatory preparation step sometimes results in needle coring, whereby the insertion of the sharp beveled needle tip into the rubber stopper on the medication vial creates a rubber "core" corresponding to the inside diameter of the needle. This rubber core can remain in the needle cannula, or can be withdrawn back into the attached syringe along with the desired medication or liquid, thereby contaminating the medication. In the worst case, the core itself can be subsequently reinjected directly into the patient's circulatory system or body tissue. Unfortunately, the size of the core makes it extremely difficult, if not impossible, to detect during normal medical procedures. Notwithstanding the small size of the core, however, standard medical practice requires the exclusion of any foreign body from a medicant or other fluid before injection. Moreover, the conventional technique of ejecting a small amount of fluid through the needle tip to eliminate contained air bubbles from the syringe does not eliminate the needle core. Prior art medical needles simply fail to address this most critical problem.

Moreover, this same problem can occur while delivering medication to a patient via an intravenous (IV) line or "piggyback" arrangement. In this situation a core can be created prior to or at the time of the insertion of the needle into the IV access port. The core can then be injected directly into the patient's system, again presenting a potentially dangerous situation during what should be the routine administration of medication to a patient. What is needed is an injection device which provides easy non-coring access to medications prior to injection, and which also ensures safe IV administration without the creation of a needle core.

An additional problem with the preliminary use of a needle to access and prepare medication for injection is the dulling of the needle that always occurs with just a single insertion of the needle into the rubber stopper on medication vials. The current solution to this problem is to change the needle after preparation of the medication and prior to injection into the patient, which is both problematic and wasteful. Removing the needle from the syringe can expose the syringe cylinder to air, and result in accidental spillage or contamination of the contents and exposure to health care workers. Moreover, most health care workers are not accustomed to this procedure, and the probability of an accidental needle stick when changing the needle only adds to their general reluctance to do so. Despite these problems, however, changing the needle is the only solution currently available.

What is needed is a time-saving, protective and economical injection device that provides separate means for accessing medication vials and for subsequently injecting patients, directly or via intravenous administration, both included in a single attachment for a syringe.

SUMMARY OF THE INVENTION

Accordingly, it is an object of the present invention to remedy the disadvantages encountered in prior art medical needles, through the provision of an injection device having a removable blunt cannula with a separately releasable vial access tip, both disposed over a sharp administration needle. The above assembly is enclosed by a removable protective sheath, to protect the vial access tip and blunt cannula (as well as the sharp administration needle nested inside the blunt cannula) before and during use.

In one embodiment the needle base of the present invention includes a Luer Lok-type attachment means for simple connection with syringes and related medical devices. After attachment of the present invention to a syringe of appropriate size, the outer protective sheath is removed by means of a minimum force. The exposed vial access tip may then be used to access medication vials and the like, with the user drawing an appropriate amount of the desired medicant through one or more openings disposed about the base of the vial access tip, which communicates with the sharp hypodermic needle nested inside the underlying blunt cannula. The fluid may then be drawn through the hollow needle and into the body of the attached syringe or related device.

The design of the vial access tip prevents the formation of a needle core upon insertion into the elastomeric stopper on a medication vial. Moreover, the vial access tip is releaseably attached to the underlying blunt cannula, and will remain in the depleted medication vial upon withdrawal of the injection assembly from the vial, thereby exposing the blunt cannula. This blunt cannula can then be used to access IV ports and the like, or alternatively it can also be removed to expose the underlying hypodermic needle for direct administration to a patient. The design of the blunt cannula tip also ensures that no needle cores will be formed upon insertion into an IV access port. In this manner the problems of needle coring and dulling are eliminated.

The protective sheath may be discarded, or, in an alternative embodiment, replaced back over the blunt cannula after accessing and withdrawing the medication. By advancing the protective sheath over the blunt cannula, both may be removed from the needle base of the present invention simultaneously, thereby exposing the underlying needle for administration purposes. It is preferred that the frictional engagement between the protective sheath and the blunt cannula after replacement of the protective sheath will have a coefficient of friction greater than that existing between the blunt cannula and the needle hub. In a preferred embodiment, the sheath, when replaced, may engage a one-way lock on the blunt cannula, for providing a contamination free surface for separating the blunt cannula from the needle hub.

Other and further objects, features, advantages and embodiments of the present invention will become apparent to one skilled in the art from reading the detailed description of the invention together with the drawings.

BRIEF DESCRIPTION OF THE DRAWINGS

FIG. 1 is a cross-sectional view of a nested assembly of the present invention.

FIG. 2 is a cross-sectional view of an assembly of the present invention with the protective sheath removed.

FIG. 3 is a cross-sectional view of an assembly of the present invention with the vial access tip detached.

FIG. 4 is a cross-sectional view of an assembly of the present invention with the blunt cannula removed.

FIG. 5 is an exploded cross-sectional view of the needle base and attachment points of the present invention.

FIG. 6 is a cross-sectional, cut away view of a vial sealed with an elastomeric stopper and containing a powdered medicament for reconstitution using an assembly of the present invention as provided in FIG. 2.

DETAILED DESCRIPTION OF THE INVENTION

As shown in FIGS. 1 and 2, the injection assembly 5 of the present invention incorporates a conventional, hollow needle or cannula 10, having a sharp, pointed tip for piercing the skin. The needle 10 can be advantageously constructed of stainless steel, but may also be constructed from any other rigid, durable material which can be formed into a sharp cannula, which is substantially nonreactive to body fluids and tissues, and which can be sterilized. It is not intended that the present invention be limited by the gauge of the needle 10 incorporated into the needle hub 11. Rather, it is contemplated that standard medical needles of various gauges can be utilized in the present invention, with the other parts of the injection assembly 5 properly sized to fit the gauge of needle 10.

The base 13 of needle 10 is mounted and sealed along its periphery to a needle hub 11 using conventional techniques known to those having skill in the art. The needle hub 11 may be constructed of metal, plastic, or any other substantially rigid, non-reactive material, sterilizable material. The needle hub 11 has an aperture 15, shown in FIG. 5, communicating with the hollow channel of the needle 10, to allow for the passage of liquid from, for example, an attached syringe or other liquid conduit, through the aperture 15 and into the hollow channel of needle 10.

As shown in FIGS. 1 and 2, the needle hub 11 most preferably includes a Luer Lok-type attachment means 12 for attaching needle 10 to syringes and other medical devices. It is not intended, however, that the invention be limited by the type of attachment means at the needle hub 11, or by the corresponding syringe or related medical device attached thereto.

Mounted over the needle 10 in injection assembly 5 is a blunt cannula 20. Blunt cannula 20 may be constructed of any appropriate metal, plastic or other substantially rigid, non-reactive, sterilizable material. The needle 10 is nested within a channel 23, which extends through the center of the blunt cannula 20 from the proximal base 22 of the blunt cannula 20 to a distal opening 26 at the opposite end of blunt cannula 20. The base 22 of the blunt cannula 20 preferably includes a means 24 for releasably sealing the channel 23 against the needle hub 11. Base 22 also preferably includes a means for preventing rotational motion of the blunt cannula 20 relative to needle hub 11. This can be accomplished by providing a button 6 on needle hub 11 which extends through slot 7 in base 22 as shown in FIGS. 1–3.

The base 22 of the blunt cannula 20 most preferably will frictionally engage and seal against the needle hub 11. This frictional seal 30 is preferably formed by molding a semi-circular rim 24 on the inside surface of base 22, which rests in and seals against a corresponding groove 14 on the needle base 11 for receiving the rim 24, as shown in FIGS. 1–2. Alternatively, an o-ring (shown as element 24' in FIG. 5) can be substituted for the rim 24, or the rim or o-ring can be placed on the needle hub 11 and the groove 14 can be placed on the inner surface of the base 22. In yet another alternative embodiment, the inner wall of base 22 can be breakably welded to, or molded as a part of, needle hub 11. Separation of blunt cannula 20 from needle hub 11 can be accomplished by twisting cannula 20 relative to needle hub 11 to fracture the joint between the base 22 of blunt cannula 20 and the needle hub 11.

As shown in FIGS. 1 and 2, hard, pointed vial access tip 21 is most preferably removably inserted in the distal opening 26 of cannula 20. Vial access tip 21 may be constructed of any appropriate material, such as metal, plastic or other substantially rigid, non-reactive materials. Vial access tip 21 can include a pointed distal end, a shaft 27 extending proximally from a base 29 of the Pointed distal end, and a retaining means 28 for frictionally securing removable tip 21 in channel 23. Vial access tip 21 is used to penetrate the membrane or stopper sealing, for example, a medication vial. Openings, such as grooves along the base 29 and/or shaft 27, or other openings between the vial access tip 21 and the distal opening 26 of blunt cannula allow for the flow of liquids through channel 23 when tip 21 is inserted in channel 23. Thus, when the vial access tip is pushed through a membrane or stopper sealing a medication vial, liquid can be drawn through channel 23 and through the needle 10.

Retaining means 28 allows for removal of tip 21 following penetration of the medication vial. Retaining means 28 can include, for example, a compressible elastomeric bead bonded to, or molded as a part of, shaft 27, as shown in FIGS. 1 and 2. Retaining means 28 could also include a host of other conventional means for frictionally holding shaft 27 in position until a force applied in a distal direction against base 29 overcomes the frictional holding force, such as an elastomeric O-ring seal in channel 23, or discontinuous beads bonded to channel 23, or even an elastomeric coating in channel 23. Most preferably, retaining means 28 permits the flow of liquid through channel 23. Thus, when the blunt cannula 20 is withdrawn from a medication bottle or the like, the covering elastomeric stopper or membrane applies a relative distal opposing force against the base 29 of the tip 21, overcoming the frictional engagement between retaining means 28 and the inside wall of channel 23 and thereby removing the vial access tip 21, which is left behind in the empty medication vial. Upon removal of vial access tip 21, the remaining assembly is as shown in FIG. 3. It would, of course, also be possible to construct a blunt cannula 20 with a fixed (i.e. non-removable) vial access tip 21. Openings at the base of the tip would permit the flow of liquid through the blunt cannula 20 and the sharp needle 10.

By using a solid pointed tip 21 to cover (and thus protect) the distal end 26 of the blunt cannula, no core can be formed. Thus, assembly 5 solves the coring problem which is found when conventional cannula and needles are used to penetrate medication bottles.

As shown in FIG. 1, a protective sheath 25 encloses the assembly 5, and is preferably releasably attached to the base 22 of the blunt cannula 20. The protective sheath 25 may be conveniently constructed of metal, plastic, or any other substantially rigid, non-reactive material. As shown in FIG. 2, when the protective sheath 25 is removed, only the blunt cannula 20 and its tip 21 are exposed, so there is no danger of accidental needle sticks. As shown in FIG. 5, protective sheath 25 is preferably provided with two separate engagements, one frictional and one locking, with the exterior of the base 22 of the blunt cannula 20. For this purpose, protective sheath 25 can be provided with a flanged base, preferably including a tongue 34, such as the square-ended tongue shown in FIG. 5. Tongue 34 can be biased towards the outer surface of cannula 20, but easily deflected away by providing a concave inner surface on the sheath 25 distal of the tongue 34. The frictional engagement mechanism of this embodiment also preferably includes a ridge 31 formed on the outer surface of cannula 20 for restraining the distal movement of sheath 25. When sheath 25 is grasped and pulled in a distal direction relative to needle hub 11, the tongue 34 will ride over ridge 31. The material selected for the protective sheath 25, and the thickness of the base of the protective sheath 25 distal of the tongue 34 will be varied so that the force required to pull tongue 34 over ridge 31 is less than the force required to overcome the frictional holding force of the seal 30 between the blunt cannula 20 and the needle hub 11.

An additional, positive locking mechanism between the protective sheath 25 and the blunt cannula 20 is desirable to enable the removal of the blunt cannula 20 from the sharp needle 10 using sheath 25. This can be accomplished, as shown in FIG. 5, by providing a ridge 32 and groove 33 proximal of ridge 31. Ridge 32 should be sufficiently high to prevent inadvertent engagement of the positive lock before it is desired to remove blunt cannula 20. Groove 33 is shaped to closely accommodate tongue 34, and is preferably cut to a depth which, in combination with the height of ridge 32, will lock the protective sheath 25 onto the blunt cannula 20, so that the force required to separate the protective sheath 25 from the blunt cannula will greatly exceed the force required to overcome the seal 30 between the base 22 of the blunt cannula 20 and the needle hub 11. While the preferred locking mechanism has been discussed, one skilled in the art will recognize that other locking mechanisms which create the appropriate level of frictional engagement between the protective sheath 25 and the base of the blunt cannula 22 can be incorporated into the present invention.

To use a device of the present invention as shown in FIG. 1 to draw liquid medicant from a vial, the user would attach the sterile assembly 5 to, for example, a syringe using the adapter 12. The plunger of the syringe should be substantially retracted into the syringe. Prior to drawing liquid medicant from a vial, the user grasps the outer surface of protective sheath 25 and pulls it away from the syringe, thus separating the protective sheath 25 from the assembly 5. The user then takes the assembly, as shown in FIG. 2, and pushes the blunt vial access tip 21 through the stopper of the medicant vial to access the sterile liquid medication inside. The plunger of the syringe is drawn out of the syringe and the vacuum imparted by this motion draws the liquid in the vial through the opening 26 in the distal end of the blunt cannula, through channel 23, through needle 10 and into the syringe. When the syringe is filled to the desired level, the blunt cannula 20 is withdrawn from the vial stopper, the blunt vial access tip 21 being drawn out of the channel 23 by the action of the elastomeric stopper material trapping the base 29 of tip 21 if the vial access tip is the preferred, removable type. (Of course, if blunt vial access tip 21 is fixed to the end of the blunt cannula 20, it will be removed with the blunt cannula). The remaining blunt cannula 20 and nested needle 10 are shown in FIG. 3.

Air which may have been trapped in the syringe can be conventionally removed by pushing the plunger in slightly to force some of the liquid medicant out of the cannula. If the user wishes to use the blunt cannula 20, for example to inject the medication into an intravenous line or the like, the user simply inserts the distal end 26 of the blunt cannula 20 into an appropriate blunt receiving adapter and injects the medication. If the user wishes to use the sharp needle 10, for example, to inject the medication directly into a patient, the user replaces the protective sheath 25 over the blunt cannula 20, pushing hard to force the tongue 34 into the groove 33. The user then pulls the protective sheath 25, which is now locked onto the blunt cannula 20, in a direction away from the syringe to overcome seal 30 and pull the blunt cannula 20 off the sharp needle 10. The medication can then be injected conventionally using the sharp needle 10.

As one skilled in the art will readily recognize, this invention has many possible applications, including use for drawing and injecting any liquid from a vial sealed with an elastomeric stopper, for drawing and injecting liquid medications from conventional medication vials, and for use in a drug reconstitution apparatus in which liquid may be injected into a vial 50 sealed with an elastomeric stopper 51 to reconstitute a powdered or dry medicament 52 as shown in FIG. 6 and as disclosed in my U.S. Pat. Nos. 5,088,996, 4,619,651, 4,516,967 and 4,185,628, which are incorporated herein by reference.

The invention has been described in terms of the preferred embodiment. One skilled in the art will recognize that it would be possible to construct the elements of the present invention from a variety of materials and to modify the placement of the components in a variety of ways. For example, seal 30 could be placed anywhere along the sloped surface of needle hub 11, so long as the seal is formed between the hub 11 and the inner surface of the blunt cannula 20. While the preferred embodiments have been described in detail and shown in the accompanying drawings, it will be evident that various further modifications are possible without departing from the scope of the invention as set forth in the following claims.

I claim:

1. A medical injection device comprising
   a substantially rigid blunt cannula having a hollow tip at a distal end and a hollow body at a proximal end, said hollow body having an inner surface shaped to receive in nested fashion a conventional hypodermic needle;
   a conventional hypodermic needle having a sharp point at one end mounted to a needle hub at an opposite end, said needle being nested in said blunt cannula with said sharp point positioned between said distal end of said cannula and said hollow body of said cannula, an outer surface of said needle hub being in contact with said inner surface of said cannula;
   a sharp vial access tip covering the hollow tip of said blunt cannula; and,
   a means for creating a seal between said blunt cannula and said nested hypodermic needle.

2. The device of claim 1 wherein said sharp vial access tip comprises a solid pointed head at one end of a shaft and wherein said shaft is inserted into and frictionally held in the distal end of said blunt cannula with said solid pointed head covering said hollow tip of said blunt cannula.

3. The device of claim 1 wherein the blunt cannula is releasably attached to the nested hypodermic needle and attached hub.

4. The device of claim 1 wherein said means for creating a seal between said blunt cannula and said hypodermic needle is a liquid-tight seal.

5. The device of claim 4 wherein the seal is located between an inner surface of a proximal end of said hollow body of said blunt cannula and an outer surface of said needle hub.

6. The device of claim 5 wherein the seal between the blunt cannula and the needle hub can be released by pulling the blunt cannula away from the needle hub.

7. The device of claim 1 additionally including a removable protective sheath which covers the blunt cannula and vial access tip and removably attaches to the blunt cannula.

8. The device of claim 7 wherein said protective sheath frictionally engages with said blunt cannula at one of a first and a second location.

9. The device of claim 8 wherein the force required to separate said protective sheath from said blunt cannula when said protective sheath is frictionally engaged with said first location is lower than the force required to separate said blunt cannula from said hypodermic needle.

10. The device of claim 8 wherein the force required to separate said protective sheath from said blunt cannula when said protective sheath is engaged at said second location is higher than the force required to separate said blunt cannula from said hypodermic needle.

11. A medical injection device, comprising:
   a. a substantially hollow, sharp needle permanently attached to a needle hub;
   b. an adapter mounted on said needle hub for attaching said needle hub to a medication delivery system;
   c. a substantially rigid blunt cannula enclosing said needle and releasably attached to said needle hub at a first end, said blunt cannula tapering to a blunt opening at a second end opposite from said first end;
   d. a sharp vial access tip attached to said opening at said second end of said blunt cannula and;
   e. a sealing means for creating a seal between said sharp needle and said blunt cannula for drawing liquid simultaneously through both said sharp needle and said blunt cannula.

12. The medical device of claim 11 wherein said adapter is a Luer Lok type connector.

13. The medical device of claim 11 wherein said adapter is for attaching said needle hub to a hypodermic syringe.

14. The medical device of claim 11 wherein said sharp vial access tip includes a solid head formed into a point, a shaft attached to a base of said head and aligned with said point, and a holding means for removably securing said shaft by friction in the second end of said blunt cannula.

15. The medical device of claim 14 whereby said holding means includes an elastomeric bead on the shaft of the sharp vial access tip, said elastomeric bead having sufficient size to extend from said shaft to bear against an inner surface of said blunt cannula.

16. The medical device of claim 11 additionally including a removable protective sheath removably attached to said blunt cannula for enclosing said blunt cannula and sharp vial access tip.

17. The medical device of claim 16 wherein said removable protective sheath includes a first locking means and wherein said first end of said blunt cannula includes a second locking means for engaging with said first locking means when said first and second locking means are pushed into engagement to lock the protective sheath and blunt cannula together, thus enabling the blunt cannula to be pulled off said needle hub, exposing said sharp needle.

18. The medical device of claim 11 wherein said blunt cannula and said needle hub are removably attached using said sealing means.

19. A method for accessing a liquid medicament contained in a vial sealed with an elastomeric stopper without the danger of creating a needle core, and subsequently administering the medicament, using an injection device which includes a substantially hollow, sharp needle permanently attached to a needle hub, an adapter mounted on said needle hub for attaching said needle hub to a syringe, a substantially rigid blunt cannula enclosing said needle and releasably attached to said needle hub at a first end using a sealing means for creating a liquid seal between the sharp needle and the blunt cannula, said blunt cannula tapering to a blunt opening at a second end opposite from said first end, and, a sharp vial access tip attached to said opening at said second end of said blunt cannula, the method comprising the steps of:
   a. attaching the injection device to a syringe using the adapter;
   b. inserting said sharp vial access tip and blunt cannula through the elastomeric stopper on the sealed vial;
   c. forcing fluid through said blunt cannula and sharp needle using said syringe as a part of the process of filling the syringe with the liquid injectant; and,
   d. withdrawing said blunt cannula from said vial, thus removing and leaving said vial access tip behind in said vial.

20. The method of claim 19 wherein the sealed vial initially contains a solid, and the liquid medicament is formed in said vial by injecting a solvent fluid into the vial using the syringe to dissolve the solid to form a solution, and wherein the solution is then drawn into the syringe for injection.

21. The method of claim 19 wherein the sealed vial contains the fluid which is used to fill the syringe.

22. The method of claim 19 additionally including the step of inserting the blunt cannula into a blunt cannula adapter on a delivery device and injecting the injectant into the delivery device.

23. The method of claim 19 additionally including the steps of removing the blunt cannula from the needle hub, thereby exposing the sharp needle, and using the sharp needle to penetrate flesh whereby the injectant can be delivered.

24. A method for accessing a liquid medicament contained in a vial sealed with an elastomeric stopper without the danger of creating a needle core, and subsequently administering the medicament, using an injection device which includes a substantially hollow, sharp needle permanently attached to a needle hub, an adapter mounted on the needle hub for attaching the needle hub to a syringe, a substantially rigid blunt cannula enclosing the needle and releasably attached to the needle hub at a first end using a sealing means for creating a liquid seal between the sharp needle and the blunt cannula, the blunt cannula tapering to a blunt opening at a second end opposite from the first end, and, a sharp vial access tip attached to the opening at the second end of the blunt cannula, the method comprising the steps of:
   a. attaching the injection device to a syringe using the adapter;
   b. inserting the sharp vial access tip and the blunt cannula through the elastomeric stopper on the sealed vial;
   c. forcing fluid through the blunt cannula and sharp needle using the syringe as a part of the process of filling the syringe with the liquid injectant;
   d. withdrawing the blunt cannula from the vial, thus removing and leaving the vial access tip behind in the vial;
   e. removing the blunt cannula from the needle hub, thereby exposing the sharp needle; and
   f. using the sharp needle to penetrate flesh whereby the injectant can be delivered.

\* \* \* \* \*